US007109267B2

(12) United States Patent
Kirby et al.

(10) Patent No.: US 7,109,267 B2
(45) Date of Patent: Sep. 19, 2006

(54) METHOD OF DISPERSING AN INSOLUBLE MATERIAL IN AN AQUEOUS SOLUTION AND AN AGRICULTURAL FORMULATION

(75) Inventors: Andrew Francis Kirby, Footscray (AU); Rodney Walter Parr, Doncaster (AU); Phillip Robert Tudor, Elwood (AU); David Hayshiv Parris, Parkville (AU)

(73) Assignee: Huntsman Surfactants Technology Corporation, Salt Lake City, UT (US)

( * ) Notice: Subject to any disclaimer, the term of this patent is extended or adjusted under 35 U.S.C. 154(b) by 0 days.

(21) Appl. No.: 10/987,094

(22) Filed: Nov. 12, 2004

(65) Prior Publication Data

US 2005/0090603 A1    Apr. 28, 2005

Related U.S. Application Data

(63) Continuation of application No. 09/529,480, filed as application No. PCT/AU98/00855 on Oct. 14, 1998, now Pat. No. 6,855,763.

(30) Foreign Application Priority Data

Oct. 14, 1997  (AU)  .................................. PO9767

(51) Int. Cl.
*B08J 5/10* (2006.01)
*C08K 13/02* (2006.01)

(52) U.S. Cl. ...................... 524/566; 524/570; 524/811; 524/819; 524/832; 504/116; 504/114

(58) Field of Classification Search ............... 524/566, 524/570, 811, 819, 832, 502, 523, 556, 572; 504/114, 116
See application file for complete search history.

(56) References Cited

U.S. PATENT DOCUMENTS

| 3,864,319 A | 2/1975 | Gaylord ................. 260/82.3 |
| 4,102,667 A | 7/1978 | Robinson et al. ............. 71/3 |
| 4,175,066 A | 11/1979 | Shibazaki et al. ..... 260/29.6 M |
| 4,191,680 A | 3/1980 | Wegmann et al. ........... 260/42 |
| 4,435,383 A | 3/1984 | Wysong ...................... 424/78 |
| 4,867,972 A | 9/1989 | Girardeau et al. ............ 424/81 |
| 5,183,574 A | 2/1993 | Hwa et al. ................. 210/701 |
| 5,476,662 A * | 12/1995 | Narayanan et al. ......... 424/409 |

FOREIGN PATENT DOCUMENTS

| EP | 201 417 B1 | 9/1988 |
| EP | 0 398 724 B1 | 8/1994 |
| EP | 0 592 169 B1 | 6/2000 |
| EP | 0 608 845 B1 | 7/2003 |
| FR | 2 397 444 | 2/1979 |
| FR | 2 545 325 | 11/1984 |
| GB | 1 414 964 | 11/1975 |
| GB | 2 087 862 A | 6/1982 |
| JP | 58-131903 | 8/1983 |
| JP | 61-236701 | 10/1986 |
| JP | 62-36302 | 2/1987 |
| JP | 62-273901 | 11/1987 |
| JP | 1-226803 | 9/1989 |
| JP | 2-111703 | 4/1990 |
| JP | 6-9302 | 1/1994 |
| WO | WO 99/18787 | 4/1999 |

OTHER PUBLICATIONS

Bognolo et al., "Polymeric Suractants and the Application in Agrochemicals Formulation," presented at the 11th Symposium of Pesticide Formulations and Application Systems in San Antonio, Texas, USA, Nov. 14-15, 1990.
Heath et al., "Stabilization of Aqueous Pesticidal Suspensions by Graft Copolymers," Advances in Pesticide Formulation Technology, Scher (ed), ACC Symp. Ser. 254, pp. 11-28, 1984.
Rogiers and Bognolo, "Novel Trends in Dispersants," Presented at the Sixth International Congress of Pesticide Chemistry, Ottawa, Canada, Aug. 10-15, 1986.
US EPA 40CFR-180, "Tolerance and Exemptions from Tolerances for Pesticide Chemical in or on Raw Agricultural Commodities," *Federal Register* 37(164):16938, Aug. 23, 1972.
Abstract of FR 2 545 325, espacenet database, Nov. 9, 1984.
Derwent WPI Acc. No. 1983-761747/198337, Abstract of JP 58-131903 A, Aug. 6, 1983.
Abstract of JP 61-236701, espacenet database, Oct. 22, 1986.
Derwent WPI Acc. No. 1987-084153/198712, Abstract of JP 62-36302 A, Feb. 17, 1987.
Abstract of JP 82 34 109, Chemical Abstracts, Feb. 24, 1982.
Abstract of JP 61-236701, Oct. 22, 1986.
Abstract of JP 1-226803, Chemical Abstracts, Sep. 11, 1989.
Abstract of JP 62-36302, Derwent Accession No. C87-035262, Feb. 17, 1987.
Derwent WPI Acc. No. 1981-65045D/198136, Abstract of JP 56089829 A, Jul. 21, 1981.
Derwent WPI Acc. No. 1982-42445E/198221, Abstract of JP 57063124 A, Apr. 16, 1982.
Derwent WPI Acc. No. 1984-111236/198418, Abstract of JP 59051963 A, Mar. 26, 1984.
Derwent WPI Acc. No. 1988-010725/198802, Abstract of JP 62273901 A, Nov. 28, 1987.
Derwent WPI Acc. No. 1993-005617/199301, Abstract of JP 4334535 A, Nov. 20, 1992.

* cited by examiner

*Primary Examiner*—Robert D. Harlan
(74) *Attorney, Agent, or Firm*—Seed IP Law Group PLLC

(57) ABSTRACT

A novel agricultural formulation includes at least one finely divided solid water-insoluble material and at least one novel dispersant containing a polymer synthesized from first and second comonomers. The first comonomer is an $\alpha,\beta$-unsaturated oxyacid or anhydride, and the second comonomer is an olefin having at least one polymerizable double bond. Also disclosed is a method for dispersing a finely divided solid insoluble material, in particular, an active water-insoluble agrochemical principal, in an aqueous solution; a method for treating a substrate with such a material or principal; and a method of making an agrochemical formulation, where the methods are based on application of the novel dispersant to the preparation of aqueous dispersions of the solid material and agrochemical principal.

35 Claims, No Drawings

METHOD OF DISPERSING AN INSOLUBLE MATERIAL IN AN AQUEOUS SOLUTION AND AN AGRICULTURAL FORMULATION

CROSS-REFERENCE TO RELATED APPLICATIONS

This application is a continuation of U.S. patent application Ser. No. 09/529,480, filed Jul. 25, 2000 (now U.S. Pat. No. 6,855,763), which application is a U.S. National Phase Application of International Application No. PCT/AU98/00855, filed Oct. 14, 1998, which application claims the benefit of Australia Patent Application No. PO 9767, filed Oct. 14, 1997, all of which are incorporated herein in their entireties.

BACKGROUND OF THE INVENTION

1. Field of the Invention

The present invention relates generally to dispersants, for use in agricultural applications, in particular the present invention relates to methods for the dispersion of insoluble material with copolymeric dispersants which dispersions are formed with improved dispersibility and show improved suspensibility. The present invention also relates to methods of producing dispersible formulations, the formulations per se and methods of treating substrates with dispersions produced from such formulations.

2. Description of the Related Art

The active principles in many agricultural applications are largely hydrophobic or water insoluble in character and are, by necessity, often administered as finely divided solids suspended in aqueous media. The majority of these active principles are manufactured and marketed in concentrated form, possibly with the addition of other insoluble inert fillers, which are then diluted prior to application. For example, the active principle is typically available in the form of a suspension concentrate (SC), wettable powder (WP) or water dispersible granule (WG). However, due to the generally hydrophobic nature of the active principle, the addition of a suitable dispersant is essential in order to achieve an homogenous dispersion with a minimum of mixing, such as may be achieved readily by hand or with minimal mechanical mixing. Furthermore, once an homogenous dispersion is achieved, the resulting suspension must remain stable for a time sufficient, at least, to allow application by usual means such as spraying. Any settling, agglomeration or flocculation of the finely divided solid may lead to inconsistent and ineffective application as well as blockage of the spraying equipment. It is therefore necessary to provide a dispersant which provides easy and homogenous dispersion and results in a suspension which maintains its stability during the application of the aqueous dispersion.

Effective dispersants for use in these applications ideally provide a suspension with acceptable dispersibility, suspensibility and lack of agglomeration. The Collaborative International Pesticides Analytical Council (CIPAC Handbook Volume 1) defines methods that can be used for determining acceptable suspensibility (MT 15.1) and degree of agglomeration (MT 59.3). For example, in suspension concentrates so-called SC formulations, this can be achieved by the addition of about 3–5 w/w % of a standard dispersant. Wettable powder (WP) and water dispersible granule (WG) formulations generally require the addition of standard dispersant in the order of 6–7 w/w % in order to achieve acceptable suspensibility and degree of agglomeration as determined by a wet sieve retention test. (MT 59.3).

Currently used dispersants for SC formulations include ethylene oxide/propylene oxide block copolymer surfactants based on an hydrophobic moiety plus ethyleneoxide. Also used are ether phosphate derivatives of non-ionic surfactants, especially of tristyrylphenol ethoxylates. Conventional anionic surfactants used include sulphonated derivatives of arylformaldehyde condensates, polyacrylates and lignosulfonates.

Dispersants for WP and WG formulations are usually limited by the requirement that the dispersant be solid at ambient temperatures, be non-gelling and not dissolve the active principle. For these reasons, conventional non-ionic surfactants are often unsuitable, and anionic dispersants are preferred. Known effective dispersants for WP and WG formulations include sulphonated alkylnaphthalene/formaldehyde condensate salts and lignosulfonate salts.

α-Olefin-polycarboxylate copolymers are well known as dispersants in a wide range of applications including pigment dispersion, emulsion polymerisation, cosmetics and pesticidal compositions. As far back as 1972 the sodium salt of a maleic anhydride and diisobutylene copolymer was given an "exemption from tolerance" for use in pesticide formulations by the United States Environmental Protection Authority following a petition from Rohm and Haas Co. FR 2545325 describes the use of ammonium and alkali metal salts of maleic anhydride-diisobutylene copolymer in pesticide granules. Similarly, EP 201417 describes the use of copolymers of maleic anhydride with surfactants selected from sulfates and phosphates of ethoxylated phenol derivatives in WP and WG formulations. JP 62036302 describes copolymers having a molecular weight range of from 5000–20000 for use with granular agrochemical compositions. Maleic anhydride and diisobutylene copolymer derivatives are described for use in conjunction with $CaCO_3$ and Mg salts for SC formulations in JP 06 09,302. The use of sulfonated derivatives of copolymers of maleic anhydride in water dispersable granules is also described in JP 58-131903.

French Patent No. 2,397,444 describes stable and concentrated dispersions of active materials which may be prepared from non-dusting powders or granular materials. It is necessary to separate the active material in the presence of a salt of an acidic resin, such as, for example, a copolymer of maleic anhydride and an α-olefinic compound; add an organic solvent which forms, together with the aqueous medium, a two-phase system; treat such two-phase system by adding a carrier substance thereto; and then isolate the product by a reduction in the volume of the organic phase by the addition of water, the solvent gradually transferring into the added water.

BRIEF SUMMARY OF THE INVENTION

We have now found that the use of certain of a range of derivatized copolymers comprising olefin monomers and α,β-unsaturated oxyacid monomers surprisingly provides improvements in dispersibility of WG formulations and suspensibility of dispersed agricultural active ingredients when compared to use of the parent copolymer. The improvement is also found surprisingly not only in alternating copolymers but in a range of other copolymers including random and block copolymers.

We have found that agriculturally acceptable salts or other water soluble derivatives of alternating copolymers for use as dispersants in agricultural compositions provide improved and consistent dispersant performance when compared to conventionally used dispersants such as sulphonated alkylnaphthalene formaldehyde condensate salts. However, we have found further derivatization not only of these copolymers but of non-alternating copolymers provides even greater improvement.

Methods for making such copolymers and derivatizations herein described will be well known to those skilled in the art of polymer synthesis.

DETAILED DESCRIPTION OF THE INVENTION

According to a first aspect of the present invention, there is provided a method of dispersing an insoluble material in an aqueous solution comprising the following steps:
  (i) providing a formulation comprising at least one insoluble material and at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents.
  (ii) dispersing said formulation in an aqueous medium.

According to a second aspect of the present invention, there is provided a method of making an agrochemical formulation comprising the steps of:
  (i) combining at least one insoluble material, and at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents;
  (ii) milling said combination to a particle size range in order to obtain a stable, readily-suspendible aqueous dispersion; and
  (iii) stabilising said aqueous dispersion to obtain an SC formulation suitable for dilution in water for agricultural use.

According to a third aspect of the present invention, there is provided a method of making an agrochemical formulation comprising the steps of:
  (i) combining at least one insoluble material, with at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents; and
  (ii) milling said combination to a desired particle size to obtain a homogeneous wettable powder (WP) formulation.

According to a fourth aspect of the present invention, there is provided a method of making an agrochemical formulation comprising the steps of:
  (i) combining at least one insoluble material suitable for agricultural use with at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents; and
  (ii) blending said combination to obtain a homogeneous wettable powder (WP) formulation.

According to a fifth aspect of the present invention, there is provided a method of making an agrochemical formulation comprising the steps of:
  (i) combining at least one insoluble material suitable for agricultural use with at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents;

(ii) agglomerating said combination to form discrete granular materials; and (iii) drying said granular materials to obtain a water dispersible granule WG formulation.

According to a sixth aspect of the present invention, there is provided a formulation produced by the process of the second, third, fourth and fifth aspects.

According to a seventh aspect of the present invention, there is provided an agricultural formulation comprising at least one insoluble material and at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents.

According to an eighth aspect of the present invention, there is provided a method of treatment of a substrate with an insoluble material comprising the following steps:

(i) preparing a formulation comprising at least one insoluble material and at least one dispersant comprising a copolymer wherein said copolymer comprises a residue of a first comonomer and a residue of a second comonomer, wherein said first comonomer is an $\alpha,\beta$-unsaturated oxyacid or anhydride and said second comonomer is an olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides; sulfonates; esters; amides; and optionally substituted pendent aromatic and heteroaromatic groups wherein said optional substituents are selected from the group consisting of sulfonates, nitrates, phosphates and other substituents derived from reaction with electrophilic reagents;

(ii) dispersing said formulation in an aqueous medium; and (iii) applying the dispersed formulation to the substrate.

The derivatisation of the copolymer is of central importance to the invention herein described. While not wishing to be bound by theory, it appears that in addition to the enhanced solubility in water, it may confer additional polarity or charge density to the dispersant such as to enhance its performance. Further it may lead to better conformational alignment of the copolymer and therefore the copolymer is more readily soluble and may more readily align itself with surfaces. We have found that a non alternating polymer which is unsuitable for use as a dispersant when used as an alkali metal or quaternary ammonium salt derivative is significantly improved in dispersant performance when derivatized according to the present invention.

The first comonomer for use in the present invention may be any comonomer polymerizable with the second comonomer. Examples of suitable preferred first comonomers of the present invention include fumaric acid, maleic acid and anhydrides, and the esters, amides and imides derived from them, itaconic acid and anhydride and the corresponding esters amides and imides derived from them, acrylic and methacrylic acids and the corresponding esters and amides derived from them, vinylphosphonic acid and the corresponding esters and amides derived from it and ethylene sulphonic acid and the esters and amides derived from it.

The second comonomer for use in the present invention is an olefin having at least one polymerizable double bond which may be substituted as defined herein.

The second comonomer for use in the second embodiment of the present invention may be an alicyclic monomer having a polymerizable exo-cyclic double bond. It will be understood that by alicyclic monomer is meant an aliphatic cyclic monomer containing moieties such as a cyclic alkyl, cyclic alkenyl or heterocyclic groups and which may comprise one or more carbocyclic or heterocyclic rings. It will be understood that by exo-cyclic is meant an alkylidene substituted cyclic structure. Alicyclic monomers having a polymerizable exo-cyclic double bond may optionally be substituted. Alicyclic monomers having a polymerizable exo-cyclic double bond of the present invention may include, for example, $\beta$-pinene, 5-ethylidene-2-norbornene, methylene cyclohexane and methylene cyclopentane. The most preferred alicyclic monomer having a polymerizable exo-cyclic double bond.

The second comonomer for use in the second embodiment of the present invention may be an alicyclic monomer having a polymerizable endo-cyclic double bond. The term alicyclic monomer is as hereinabove defined. It will be understood that by endo-cyclic is meant the polymerizable double bond has both ends (or termini) forming part of the cyclic structure of the alicyclic monomer. Alicyclic monomers having a polymerizable endo-cyclic double bond may optionally be substituted. Alicyclic monomers having a polymerizable endocyclic double bond may include substituted and unsubstituted norbornene, cyclopentadiene and substituted cyclopentadienes, substituted and unsubstituted dicyclopentadienes, cyclohexenes, furans and indenes. Most preferred of the above monomers containing an endo-cyclic double bond are dicyclopentadiene and dimethyldicyclopentadiene.

The second comonomer for use in the second embodiment of the present invention may be an $\alpha$-olefin having at least one cyclic substituent. It will be understood that by $\alpha$-olefin is meant an olefinic compound having a terminal double bond. Suitable cyclic substituents include benzene and substituted benzene, cyclopentane, cyclohexane, and other cycloaliphatics, heterocyclics, heteroaromatics, aromatics and polyaromatics. Examples of suitable $\alpha$-olefinic cyclic compounds include limonene and similar terpenes, vinyl cyclohexanes, vinyl cyclohexenes, vinyl pyridines, vinyl thiophenes, vinyl naphthalenes, vinyl furans, vinyl pyrans and, vinyl pyrrolidones. Most preferred $\alpha$-olefin cyclic monomers include limonene, vinyl naphthalene, vinyl pyrrolidone, allyl glycidyl ether and vinyl cyclohexene.

The second comonomer of the second embodiment of the present invention may be an α-olefin having an alkyl group such as diisobutylene, isobutylene, n-octene, n-decene, allyglycidylether or vinylisobutylether. The second comonomer may also be an internal olefin.

Preferred examples of the first comonomer may be described as having structure I:

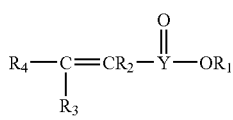

I wherein $R_1$ is a metal, quaternary ammonium, phosphonium or sulphonium residue, $R_2$ is hydrogen, $C_1$ to $C_4$ alkyl or $CH_2CO_2H$, Y is a carbon atom, the group O=S, or the group POR where R is a hydrogen atom or alkyl radical having from 1 to 10 carbon atoms (or carboxylated such radical), $R_3$ is hydrogen and $R_4$ is hydrogen, an alkyl radical or a carboxylic acid derivative of form II:

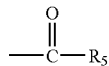

II wherein $R_5$ is $OR_6$, $NR_6R_7$ or $SR_6$, wherein $R_6$ and $R_7$ are hydrogen, alkyl, O-alkyl, or alkyl groups with a hetero atom substituent. The second comonomer may be alternatively described as a residue having formula III:

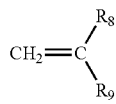

III wherein $R_8$ represents hydrogen, or a straight or branched chain alkyl of from 1–4 carbon atoms, $R_9$ represents hydrogen, a branched chain alkyl radical of from 1–12 carbon atoms, or a cycloalkyl radical, and/or a vinyl compound of formula IV:

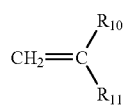

IV wherein $R_{10}$ is hydrogen or a straight or branched chain alkyl radical of from 1–4 carbons and $R_{11}$ is given by formula V, VI or VII:

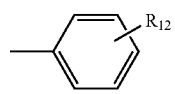

V

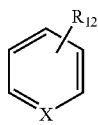

VI

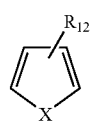

VII wherein $R_{12}$ represents one or more alkyl radicals or one or more of H, Cl, OR, $SO_3R_1$ $NO_2$ and $PO_3R_1$, and X is a hetero atom other than carbon; and/or an olefin shown by formula VIII:

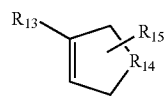

VIII wherein $R_{13}$ is Cl, $SO_3R_1$, alkyl, O-alkyl or O-aryl, $R_{14}$ represents from 4–20 carbon atoms such as to make a cyclic or polycyclic alkane or polyalkenyl compound, and $R_{15}$ is an epoxide or $SO_3R_1$ reacted with an unsaturated portion of the ring comprising $R_{14}$; and/or an exocyclic olefin shown by formula IX:

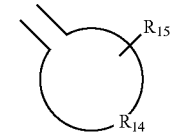

IX and/or an internal olefin shown by formula X:

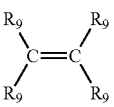

X where $R_9$ is the same or different and as hereinabove defined.

The dispersant copolymers of the present invention may also include copolymers being the water soluble derivatives of a combination of an unsaturated α,β-unsaturated oxyacid or anhydride and another olefinic monomer, not limited to being of an alternating structure, that may have been derivatized post copolymerisation such as to provide the necessary substituents which may enhance water solubility and regularity of charge or polarity on the polymer. Such derivatization includes that obtained from reaction of groups pendant to the copolymer such as acids and acid derivatives with nucleophilic reagents such as alcohols, amines and thiols to give esters, amides and thioesters respectively.

In a further form of derivatization copolymers with residual reactive unsaturation may be reacted with electrophilic or radical reagents such as peroxides or sulphite to give epoxides and sulphonates respectively.

In a special case of the above, copolymers with pendant aryl or heteroaryl groups can be made to undergo electrophilic aromatic substitution with sulphonating, nitrating and phosphating reagents.

While not wishing to be bound by theory, copolymers with hydroxyl groups can be esterified with acids including carboxylic, sulphuric and phosphoric acids. The alternating, or repeating, units are preferably monomers but may also be dimers, trimers or small oligomers.

While not wishing to be bound by theory, it is believed that the stiffness of the polymer molecule is relates to its performance as a dispersant. It is believed that improved dispersant performance is related to the degree of steric hindrance and the resistance of copolymer to free rotation.

The copolymer may contain additional comonomer residues. For example, the addition of a small amount, say less than 10%, of methyl methacrylate will not substantially change the character of the derivatized copolymer. The copolymer may contain residues of additional olefin comonomers whether derivatized or not. Suitable copolymers for use in the present invention also include copolymers of three or more comonomers. Additional comonomers may also be incorporated into the derivatized copolymer without changing the character of the polymer.

While not wishing to be bound by theory it appears that where a consistent hydrophobic polymer backbone is provided in the presence of regularly spaced anionic charge or steric barrier along the polymer, the improved dispersant performance is preserved.

The preferred molecular weights of the copolymers of the present invention are in the range of from 1000 to 90000 daltons. We have found that certain higher molecular weight copolymers show a certain degree of intractability in solution and our more preferred range is from 1000–30000 daltons, even more preferred is 1000–10000 daltons.

We have found that agriculturally acceptable salts of copolymers as described herein for use as dispersants in agricultural compositions provide improved and consistent dispersant performance when compared to conventionally used dispersants such as sulfonated alkylnaphthalene formaldehyde condensate salts.

It is surprising that copolymers as described herein give enhanced performance when compared to previously described dispersants structures in the prior art such as for example diisobutylene, isobutylene and styrene copolymers with maleic anhydride while still other derivatives described in those same publications, cannot be reasonably used as dispersants in agricultural applications at all. For example we have found that styrene-maleic anhydride copolymer derivatives resulted in a less stable and sometimes unstable dispersion. Further, copolymers of methylvinylether and maleic anhydride also afford an unstable dispersion. Similarly some linear α-olefin maleic anhydride derivatives such as those derived from n-octene and n-decene also yielded unstable dispersions affording poor suspensibility. It was found that the substituted or derivatized copolymers of the above copolymers according to the present invention showed improved performance not limited by possible effects of molecular weight and/or molecular conformation which appear to limit the performance of the parent copolymer.

The performance of the copolymers described herein has been observed at different dispersant concentrations in WP and WG formulations to exhibit improved storage stability. Also we have found that in many cases it is possible to lower the dispersant concentration from normally accepted levels and retain an acceptable suspensibility result, thereby achieving more efficient the surface coverage of the dispersant. In practical terms this means the dispersant will be more cost effective to the end user. When the use rate of copolymers is compared to that of a diisobutylene maleic anhydride sodium salt of similar molecular weight typically we have found that the copolymers of this invention may give acceptable stability at a concentration lower than the corresponding diisobutylene derivative. In addition the formulations typically show improved dispersibility. When compared to sulfonated alkyl naphthalene formaldehyde condensates, suspensibility is significantly improved, even at lower concentrations.

Methods for making such copolymers of the second embodiment of the present invention from first and second comonomers will be well known to those skilled in the art of polymer synthesis. The comonomers of the present invention may be substituted prior to or post polymerization with methods which will be appreciated by those skilled in the art.

The dispersant system used in embodiments of the present invention may be a mixture of the copolymer as herein described with other dispersants known to those skilled in the art, including alkyl substituted and unsubstituted sulfonated naphthalene formaldehyde condensate salts, alkyl substituted and unsubstituted phenol formaldehyde condensate salts, lignosulphonate salts, polyacrylate salts, and previously described α-olefinic unsaturated dicarboxylic acid copolymer derivatives.

In agrochemical applications, a wide variety of insoluble materials such as active principals are delivered in aqueous suspension. Active principals such as those used in WP, WG and SC formulations are generally insoluble at ambient temperatures. Water insoluble materials which may advantageously be used in WP, WG and SC formulations include herbicides, insecticides, fungicides, biocides, molluscicides, algaicides, plant growth regulators, anthelmintics, rodenticides, nematocides, acaricides, amoebicides, protozoacides, crop safeners and adjuvants. Examples of such actives commonly granulated or made as powders in agriculture include: triazine herbicides such as simazine, atrazine, terbuthylazine, terbutryn, prometryn and ametryn, urea herbicides such as diuron and fluometron, sulphonyl urea herbicides such as chlorsulfuron, metsulfuron methyl, nicosulfuron and triasulfuron, sulphonanilide herbicides such as flumetsulam, organophosphate insecticides such as azinphos methyl, chlorpyrifos, sulprofos and azamethiphos, carbamate insecticides such as aldicarb, bendiocarb, carbaryl and BPMC, synthetic pyrethroids such as bifenthrin, as well as various types of fungicides including dimethomorph, benomyl, carbendazim, mancozeb, triazoles such as hexaconazole and diniconazole, acaricides such as propargite. A list of such products can be drawn from the Pesticide Dictionary (contained in the Farm Chemicals Handbook) or the British Crop Protection Society: Pesticides Manual.

In addition, some fertilizers and also water soluble active principles may use water dispersible formulations either by addition of inert carriers for convenience in handling or to aid in a controlled release formulation.

A wide variety of other insoluble materials are used in agricultural applications including fillers and carriers, for example but not limited to, natural and synthetic silicates and silicate minerals, mineral oxides and hydroxides and also natural and synthetically derived organic materials. Such materials may be added as porous carriers, as moisture inhibition agents, to aid binding or agglomeration properties of a formulation or simply to fill a formulation to a convenient weight. Examples of such fillers may include natural silicates such as diatomacious earth, synthetic precipitated silicas, clays such as kaolin, attapulgites and bentonites, zeolites, titanium dioxide, iron oxides and hydroxides, aluminium oxides and hydroxides, or organic materials such as bagasse, charcoal, or synthetic organic polymers. These other insoluble materials may be readily dispersed in accordance with the present invention.

An additional agent conventionally used in combination with dispersants used in the above formulations is a surfactant wetting agent. The role of the wetting agent in the case of SC formulations is to aid removal of air from particle surfaces during manufacture and to aid dilution in water. In the case of WP formulations the role of the wetter may be to aid penetration of the solids into water, while in the case of WG formulations it may aid penetration of the granules into water and aid disintegration of granules back to primary particle size. In some cases the dispersant may itself function as a suitable wetting agent while in others the dispersant may show an antagonistic effect on the wetter. As a further embodiment of the present invention at least one surfactant wetting agent may be selected from the group consisting of an alkylpolysaccharide; di or mono alkyl sulphosuccinate derivative; a nonionic surfactant loaded onto an inert silicate carrier; and a non-ionic surfactant delivered in the form of a urea surfactant complex.

The step of dispersing the formulation in an aqueous medium may be achieved by any convenient means dependent on the nature of the formulation. It is desirable that the dispersion of the formulation in an aqueous solution may be conducted either by hand or with a minimum of mechanical agitation. Mechanical agitation may include stirring, mixing, blending and other similar processes.

The suspension of insoluble material in aqueous medium will be typically used for the treatment of a substrate such as plant or other agricultural medium. The application of the suspension onto the substrate may be achieved by any convenient means, including spraying, and the like. Granules are generally dispersed in water prior to being sprayed by the farmer. Farm sprays may be as a small back-pack handspray or a large boom spray or other convenient means. Aerial spraying is also sometimes used.

Formulations of the present invention may also be applied to the substrate directly, prior to dispersion. The subsequent application of rain or other aqueous media is sufficient for the formulation of the suspension of particulate material.

The present invention is described with reference to WP, WG and SC formulations. In each case, formulations provide a stable aqueous dispersion of finely milled insoluble hydrophobic particles. The stability properties of the dispersion and hence the effectiveness of the dispersion can be measured by means of a suspensibility test as described by the CIPAC test MT 15.1. In this test the volume fraction of suspended material is compared to that which has settled out due to gravity after 30 minutes. Typically a reported percentage suspersiblity about 80% would be considered as an effective dispersant for WG and WP formulations, while in excess of 90% would be expected for an SC formulation. Another measure of the stability of the dispersion is the degree to which particles remain non aggregated. This may also be a property of the even distribution of the dispersant in the formulation. The degree to which particles may be aggregated is often measured by a wet sieve retention test as described in CIPAC test MT 59.3. In this test the dispersed solid is poured through a series of fine sieves and retained material is measured as a fraction of the total amount of dispersed material. Formation of such aggregates is a major problem observed in WG formulations and to a lesser extent in WP formulations.

Generally WP formulations are produced by milling the active principle either alone or in combination with fillers, dispersants and/or surfactant wetters to a suitable particle size, typically in the 5–15 µm range. The milled material is then dry blended with a surfactant wetter, and/or dispersant if not already present or with additional dispersants and/or surfactant wetters to give a homogeneous composition. The powder formulation is assessed for wettability according to a method such as CIPAC MT 53.5.1 and suspensibility as per CIPAC MT 15.1. A formulation will desirably have a wettability of less than 1 minute and a suspensibility above 80%. Below 60% would generally be considered unacceptable. Results which might be commercially acceptable are either determined by the local registration authority or by the standards set by the formulators themselves.

In the case of WG formulations a suitably milled active ingredient with or without other fillers, typically of particle size 5 to 15 µm, may be mixed with one or more surfactant wetters and one or more dispersants. Typically an excess of water is added to bind the particles together into agglomerates. The excess water is later reduced by suitable air drying techniques to an optimal level.

The agglomerates are typically granulated using one of many techniques including pan granulation, drum granulation, fluid bed granulation, spray drying, tableting or extrusion techniques which are well known to those skilled in the art.

The wetter and dispersant may either be powder blended with the active ingredient or alternatively blended as an aqueous solution in the water used to aid agglomeration. The active ingredient, fillers, wetter and dispersant may also be milled together in one operation prior to addition of water.

For a WG formulation to be acceptable an additional requirement is that the said granules should readily disperse in water back to the primary dispersed particle size within a short period. This property is known as dispersibility and in describing the current invention it is measured as the time taken for granules to disperse back to primary particle size in water under a standard degree of agitation. A dispersion time of less than one minute is desirable, 20 seconds is excellent and 2 minutes is poor. Desirably the granules should also have good suspensibility. Suspensibility is typically tested using CIPAC MT 15.1. Above 80% is a desirable result, less than 60% is generally regarded as undesirable. In many cases when testing granules a so-called maximum surface coverage result is often obtained. This is where the suspensibility results reach a maximum level then plateau. Adding more dispersant will not generally improve the result. This phenomenon is thought to be due to the particle size distribution of the material. Usually there is a given number of particles which are of such a size that they will settle regardless of type and concentration of dispersant.

Desirably the granules should have low wet sieve retention. Wet sieve retention is typically tested using CIPAC MT 59.3. For the 150 µm sieve less than 0.1% retained material is desirable. Less than 0.02% is more desirable. Likewise for the 53 µm sieve less than 0.6% is desirable, anything less than this is more desirable.

A further desirable property of a WG formulation is that the granules should be non-dusty and resistant to attrition. This is often a property of the method of granulation used and the level of compaction there obtained. Often there is an observed tradeoff between the dispersibility properties of a WG formulation and the level of compaction and attrition resistance. Attrition resistance may be measured by subjecting granules to a set degree of agitation and measuring the level of smaller particles generated by means of passing through sieves of various sizes.

Storage stability may be tested by storage at 50° C. and tested as above at 1 month and 3 month intervals to determine if any properties have changed significantly.

Preferably, the granules should maintain these properties on storage. Surprisingly, it has been observed that, upon prolonged storage, solid formulations such as WP and WG formulations containing dispersants such as those described herein are not as susceptible to deterioration in dispersability and suspensibility as formulations of the prior art.

We have also found that WP and WG formulations which incorporate the dispersants described herein require typically less dispersant, than for presently known WP and WG formulations.

As a further embodiment of the present invention in the case of WP and WG formulations the dispersants herein described may be combined with surfactant wetting agents selected from the classes comprising alkylpolysaccharides, dialkyl and monoalkylsulphosuccinate salts, nonionic surfactants loaded onto porous silicate carriers and urea surfactant complexes of non-ionic surfactants. The wetting agent may be combined in such formulations at a rate in excess of 1% w/w and preferably less than 3% w/w. Most preferred from the alkylpolysaccharide class of wetting agents are alkylpolyglucosides derived from reaction with glucose and a primary hydrocarbon alcohol. Even more preferred are the highly crystalline derivatives such as obtained from ECOTERIC AS 20 and ECOTERIC AS 10 (Huntsman Corporation Australia Pty Ltd). Most preferred from the monoalkylsulphosuccinate class are sodium or potassium salts of cyclohexyl, iso-octyl and n-octyl sulphosuccinate. Most preferred from the dialkylsulphosuccinate class are sodium or potassium salts of dicyclohexyl, diisooctyl and di-n-octyl sulphosuccinates. Most preferred from the class of nonionic surfactants loaded onto insoluble porous silicate carriers are ethoxylated surfactants loaded onto carriers such as TERIC 157 (Huntsman Corporation Australia Pty Ltd). Most preferred wetting agents from the urea surfactant complexes are urea adducts of alcohol ethoxylate surfactants such as TERWET 7050 (Huntsman Corporation Australia Pty Ltd). The wetters herein described show good wettability and dispersibility for the formulations and have the additional advantage of showing storage stability in combination with the copolymer dispersants described. Whereas by comparison some commonly used WG and WP wetters such as alkylnaphthalene sulphonate salts and lignosulphonate salts have been found to show poor storage stability.

In the case of SC formulations in the present invention an active ingredient is typically added to water containing a dispersant, preferably with a surfactant wetting agent together with a conventional non-ionic dispersant. A humectant may also be included. A dispersion is formed using high shear mixing. The dispersion is then milled by any one of several means of wet milling so that the mean particle size of the dispersed solid is below 5 µm more typically in the range of from 1 to 3 µm. The resulting product is known as a millbase and may be modified with additives such as antifreeze, thickeners and antisettling agents, biocides and colouring agents may be added. For an SC formulation to be acceptable it should not show a high degree of thickening, settling or growth of aggregates over time. These physical properties can be assessed by visual observation.

SC's generally require good viscosity and storage stability. Storage stability is usually assessed as degree of top settling or syneresis, sedimenting or "claying" which is the tendency to form a sticky layer on the bottom and "bleeding" which is the tendency of the dispersion to separate without necessarily displaying even settling. Redispersibility is also important. These may also be assessed visually.

For SC formulations in the case of dispersants described herein only certain dispersant copolymers are suitable. When used alone, some dispersant copolymer derivatives give a viscosity of slurry premix unsuitable for milling so it is preferable to combine the dispersant with another fast acting well known dispersant such as an EO/PO block co-polymer type dispersant. While not wishing to be bound by theory it appears that the dispersant needs time to migrate to the surface of the dispersed particles. The dispersant copolymers are used synergistically with other known dispersants in some cases.

While the present invention has been described with reference to agrochemical formulations, it will be apparent that the improvements in dispersibility and suspensibility will render the present invention useful in other applications. The present invention will now be further described with reference to the following non-limiting examples and figures. All percentages recited herein are by weight of the total composition unless otherwise specified.

EXAMPLES

Example 1

A simazine 900 g/kg WG Formulation of the following composition was prepared:

| | |
|---|---|
| Simazine tech. (98% w/w) | 91.8% w/w |
| MORWET EFW (Witco Corp.) | 1.5 |
| DISPERSANT | 6.2 |
| Water | 0.5% |

The dispersant used was an alkylnaphthalene formaldehyde condensate salt, SCS 2258 (ICI Surfactants). The granules were prepared by blending the solids with approximately 15% by weight of water such as to give a plastic premix which was then extruded using a Fuji-Paudal laboratory scale extrusion granulator. The resulting granules were then dried by means of a fluid bed drier back to a water content of approximately 0.5% w/w.

The resulting WG was tested for dispersibility by recording the time in seconds required for total disintegration under uniform agitation. The suspensibility was tested according to CIPAC MT 15.1 and the wet sieve retention was tested using 150 micron and 53 micron sieves according to CIPAC MT 59.3. Results are recorded in TABLE 1.

Example 2

A simazine 900 g/Kg WG was prepared and tested as described in example 1 where the dispersant used was POLYFON H (Westvaco Corp), a lignosulphonate salt. The results are described in TABLE 1.

Example 3

A Simazine 900 g/kg WG formulation of the following composition was prepared:

| | |
|---|---|
| Simazine tech. (98% w/w) | 91.8% w/w |
| ATPLUS G73050 (now sold under the trademark TERWET 7050, Huntsman Corporation Australia Pty Ltd) | 1.5 |
| DISPERSANT | 3.1 |
| Kaolin | 3.1 |
| Water | 0.5% |

The dispersant used was the sodium salt of an alternating copolymer of n-octene and maleic anhydride of approximate molecular weight 20,000 to 30,000. The granules were prepared and tested in the manner described in Example 1. The results are shown in TABLE 1.

Example 4

A Simazine 900 g/kg WG formulation was prepared and tested in the manner described in Example 3 with the dispersant being the sodium salt of a copolymer of n-decene and maleic anhydride. Results are shown in TABLE 1.

Example 5

A Simazine 900 g/kg WG formulation was prepared and tested in the manner described in Example 3 with the dispersant being the sodium salt of a copolymer of diisobutylene and maleic anhydride of approximate molecular weight 20,000 to 30,000. Results are shown in TABLE 1.

Example 6

A WG formulation was prepared and tested as described in Example 3 with the dispersant being the sodium salt of SMA 1000 (Atochem Inc) which is a 1:1 molar ratio copolymer of styrene and maleic anhydride. Results are shown in TABLE 1.

Example 7

A WG formulation was prepared and tested as described in Example 3 with the dispersant being the sodium salt of SMA 3000 (Atochem Inc) which is a 3:1 molar ratio copolymer of styrene and maleic anhydride. Results are shown in TABLE 1.

Example 8

A WG formulation was prepared and tested as described in Example 3 with the dispersant being the sodium salt of GANTREZ AN 119 resin (Rhodia Inc) which is a copolymer of methylvinyl ether and maleic anhydride. Results are shown in TABLE 1.

Example 9

A Simazine 900 g/kg WG formulation of the following composition was prepared:

| | |
|---|---|
| Simazine tech. (98% w/w) | 91.8% w/w |
| ATPLUS G73050 (now sold under the trade mark TERWET 7050, Huntsman Corporation Australia Pty Ltd) | 1.5 |
| DISPERSANT | 3.1 |
| Kaolin | 3.1 |
| Water | 0.5% |

The dispersant used was the sodium salt of a copolymer of n-octene and maleic anhydride derivatized by reaction with morpholine to give a morpholine amide derivative. The granules were prepared and tested in the manner described in Example 1. Results are shown in TABLE 2.

Example 10

A Simazine 900 g/kg WG formulation was prepared and tested in the manner described in Example 9 with the dispersant being the sodium salt of the morpholine amide derivative of a co-polymer of n-decene and maleic anhydride. Results are shown in TABLE 2.

Example 11

A Simazine 900 g/kg WG formulation was prepared and tested in the manner described in Example 9 with the dispersant being the sodium salt of the morpholine amide derivative of SMA 1000 (Atochem Inc), a 1:1 molar ratio copolymer of styrene and maleic anhydride. Results are shown in TABLE 2.

Example 12

A Simazine 900 g/kg WG formulation was prepared and tested in the manner described in Example 9 with the dispersant being the sodium salt of the morpholine amide derivative of SMA 3000 (Atochem Inc), a 3:1 molar ratio copolymer of styrene and maleic anhydride. Results are shown in TABLE 2.

Example 13

A Simazine 900 g/kg WG formulation was prepared and tested in the manner described in Example 9 with the dispersant being the sodium salt of the aromatic sulphonated derivative of SMA 1000 (Atochem Inc), a 1:1 molar ratio copolymer of styrene and maleic anhydride. Results are shown in TABLE 2.

Example 14

A Simazine 900 g/kg WG formulation was prepared and tested in the manner described in Example 9 with the dispersant being the sodium salt of the co-polymer of alphamethylstyrene and maleic anhydride derivatized with ammonia to give the corresponding monoamide. Results are shown in TABLE 2.

Example 15

A Simazine 900 g/kg WG formulation was prepared and tested in the manner described in Example 9 with the dispersant being the sodium salt of the copolymer of alphamethylstyrene and maleic anhydride derivatized with ethanolamine to give the corresponding ethanolamide. Results are shown in TABLE 2.

Example 16

A Simazine 900 g/kg WG formulation was prepared and tested in the manner described in Example 9 with the dispersant being the sodium salt of the copolymer of alpha-methylstyrene and maleic anhydride derivatized with n-butylamine to give the corresponding n-butylamide. Results are shown in TABLE 2.

Example 17

A Simazine 900 g/kg WG formulation was prepared and tested in the manner described in Example 9 with the dispersant being the sodium salt of the copolymer of alpha-methylstyrene and maleic anhydride derivatized with morpholine to give the corresponding morpholine amide. Results are shown in Table 2.

Example 18

A Simazine 900 g/kg WG formulation was prepared and tested in the manner described in Example 9 with the dispersant being the sodium salt of the copolymer of dicyclopentadiene and maleic anhydride derivatized morpholine to give the corresponding amide. Results are shown in TABLE 2.

Example 19

A Simazine 900 g/kg WG formulation was prepared and tested in the manner described in Example 9 with the dispersant being a sulphonated derivative of the sodium salt of the copolymer of dicyclopentadiene and maleic anhydride. Results are shown in TABLE 2.

Example 20

A Simazine 900 g/kg WG formulation was prepared and tested in the manner described in Example 9 with the dispersant being a sulphonated derivative of the sodium salt of the copolymer of dimethyldicyclopentadiene and maleic anhydride. Results are shown in TABLE 2.

Example 21

A Simazine 900 g/kg WG formulation was prepared and tested in the manner described in Example 9 with the dispersant being the sodium salt of the copolymer of dimethyldicyclopentadiene and maleic anhydride derivatized with morpholine to give the corresponding morpholine amide. Results are shown in TABLE 2.

Example 22

A Simazine 900 g/kg WG formulation was prepared and tested in the manner described in Example 9 with the dispersant being the sodium salt of the morpholine amide derivative of Gantrez AN119 (Rhodia Corp.), a copolymer of methylvinyl ether and maleic anhydride Results are shown in TABLE 2.

Example 23

A Simazine 900 g/kg WG formulation was prepared and tested in the manner described in Example 9 with the dispersant being the sodium salt of the cyclohexyl amide derivative of Gantrez AN119 (Rhodia Corp), a copolymer of methylvinyl ether and maleic anhydride Results are shown in TABLE 2.

Example 24

An Atrazine 900 g/Kg SC formulation of the following composition was prepared.

| | |
|---|---|
| Atrazine tech. 97% w/w | 51.5% w/v |
| Monoethylene glycol | 4.0 |
| DISPERSANT | 4 |
| Silicone antifoam | 0.2 |
| Rhodopol 23 (Rhodia Inc.) | 0.2 |
| Proxel GXL 20 (Zeneca plc) | 0.1 |
| Water. | 55.0 |

The dispersant used was the sodium salt of a sulphonated copolymer of dicyclopentadiene and maleic anhydride. The SC was prepared by dissolving the monoethylene glycol, ATLOX 4896A and DISPERSANT in 85% of the water and adding the Atrazine tech and antifoam with vigorous mixing to form a slurry or millbase premix. The premix is then milled using a Dynomill laboratory scale bead mill to give a suitable particle size distribution of >98% of particles below 5 microns. The millbase thus obtained was then blended with Proxel GXL 20(Zeneca plc) and Rodopol 23(Rhodia Inc.) in a premix and then made up to the desired volume with the remaining water and mixed to a homogeneous mixture. The SC thus obtained was of usable viscosity and was found to be storage stable after storage at 2 degrees C. and 50 degrees C. for one month, with minimal syneresis and thickening and no claying, sedimentation or aggregates being observed.

TABLE 1

WDG Results from Prior Art

| Example No. | Dispersibility (Seconds) | | | Suspensibility (%) | | | Wet Sieve Retention (%) | | | | | |
|---|---|---|---|---|---|---|---|---|---|---|---|---|
| | | | | | | | 150 μm | | | 50 μm | | |
| | $T_0$ | $T_1$ | $T_3$ | $T_0$ | $T_1$ | $T_3$ | $T_0$ | $T_1$ | $T_3$ | $T_0$ | $T_1$ | $T_3$ |
| 1 | 52 | 46 | 44 | 82 | 63 | 69 | 0.087 | 0.41 | 2.2 | 0.033 | 1.53 | 1.70 |
| 2 | 58 | 45 | 46 | 80 | 68 | 70 | 0.029 | 1.09 | 0.92 | 0.486 | 4.10 | 4.70 |

TABLE 1-continued

WDG Results from Prior Art

| Example No. | Dispersibility (Seconds) | | | Suspensibility (%) | | | Wet Sieve Retention (%) | | | | | |
|---|---|---|---|---|---|---|---|---|---|---|---|---|
| | | | | | | | 150 μm | | | 50 μm | | |
| | $T_0$ | $T_1$ | $T_3$ | $T_0$ | $T_1$ | $T_3$ | $T_0$ | $T_1$ | $T_3$ | $T_0$ | $T_1$ | $T_3$ |
| 3 | 36 | — | — | 39 | — | — | — | — | — | — | — | — |
| 4 | 33 | — | — | 59 | — | — | 0.002 | — | — | 0.042 | — | — |
| 5 | 60 | 54 | 50 | 72 | 78 | 71 | 0.02 | 0.02 | 0.016 | 0.15 | 0.21 | 0.28 |
| 6 | 55 | — | — | 31 | — | — | 0.027 | — | — | 0.095 | — | — |
| 7 | >280 | — | — | <10 | — | — | — | — | — | — | — | — |
| 8 | 53 | — | — | 48 | — | — | 0.002 | — | — | 0.085 | — | — |

$T_0$ initial results
$T_1$ after 1 month storage at 50° C.
$T_3$ after 3 months storage at 50° C.

TABLE 2

WG Formulations using Dispersants of Second Embodiment

| Example No. | Dispersibility (seconds) | | Suspensibility (%) | | Wet Sieve Retention (%) | | | |
|---|---|---|---|---|---|---|---|---|
| | $T_0$ | $T_1$ | $T_0$ | $T_1$ | $T_0$ | $T_1$ | $T_0$ | $T_1$ |
| 9  | 71 | 45  | 87 | 82 | 0.10  | 0.10  | 0.068 | 0.21  |
| 10 | 95 | 85  | 75 | 68 | 0.005 | 0.001 | 0.042 | 0.051 |
| 11 | 67 | 62  | 85 | 83 | 0.005 | 0.002 | 0.060 | 0.118 |
| 12 | 28 | 26  | 84 | 88 | 0.001 | 0.005 | 0.039 | 0.052 |
| 13 | 58 | 56  | 85 | 83 | 0.038 | 0.068 | 0.195 | 0.140 |
| 14 | 68 | 68  | 83 | 83 | 0.001 | 0.004 | 0.051 | 0.054 |
| 15 | 10 | —   | 70 | —  | 0.05  | —     | 2.79  | —     |
| 16 | 68 | 40  | 81 | 77 | 0.005 | 0.012 | 0.044 | 0.092 |
| 17 | 53 | 120 | 86 | 81 | 0.005 | 0.21  | 0.065 | 0.13  |
| 18 | 40 | 32  | 87 | 85 | 0.004 | 0.007 | 0.051 | 0.313 |
| 19 | 26 | 33  | 86 | 86 | 0.001 | 0.001 | 0.045 | 0.053 |
| 20 | 57 | 44  | 85 | 86 | 0.002 | 0.008 | 0.064 | 0.199 |
| 22 | 57 | 36  | 87 | 72 | 0.02  | 0.55  | 0.06  | 5.64  |
| 23 | 69 | 95  | 86 | 83 | 0.033 | 0.033 | 0.144 | 0.88  |
| 21 | 32 | 30  | 87 | 87 | 0.001 | 0.005 | 0.054 | 0.048 |

$T_0$ initial results
$T_1$ after 1 month storage at 50° C.
*Data not yet available
— Testing discontinued Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

The invention claimed is:

1. A method of dispersing a solid active water-insoluble agrochemical principal in an aqueous solution comprising the following steps:
   (i) providing a formulation comprising at least one finely divided solid active water-insoluble agrochemical principal and at least one dispersant comprising a water soluble copolymer wherein said copolymer comprises a residue of a first comonomer and a residue of a second comonomer, wherein said first comonomer is acrylic or methacrylic acid and said second comonomer is an α-olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides, sulfonates, esters, amides, and optionally substituted pendent aromatic and heteroaromatic groups wherein said optional substituents are selected from the group consisting of sulfonates, nitrates, phosphates and other substituents derived from reaction with electrophilic reagents; with the provisos that (a) when the second comonomer is sulphonated styrene or sulphonated isobutylene, the first comonomer is substituted, (b) when one of the first and second comonomers is substituted with an ester group containing a polvalkyleneoxy moiety, the other of the first and second comonomers must be substituted and (c) when the second comonomer is sulphonated styrene, the first comonomer is not alkyl acrylate or alkyl methacrylate; and
   (ii) dispersing said formulation in an aqueous medium to form a suspension of the at least one active water-insoluble agrochemical principal.

2. A method of dispersing a solid active water-insoluble agrochemical principal in an aqueous solution comprising the following steps:
   (i) providing a formulation comprising at least one finely divided solid active water-insoluble agrochemical principal and at least one dispersant comprising a water soluble copolymer wherein said copolymer comprises a residue of a first comonomer and a residue of a second comonomer, wherein said first comonomer is an α,β-unsaturated oxyacid or anhydride and said second comonomer is an α-olefin having at least one polymerizable double bond and at least one cyclic substituent selected from benzene and substituted benzene, and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides, sulfonates, esters, amides, and optionally substituted pendent aromatic and heteroaromatic groups wherein said optional substituents are selected from the group consisting of sulfonates, nitrates, phosphates and other substituents derived from reaction with electrophilic reagents; with the provisos that (a) when the second comonomer is sulphonated styrene or sulphonated isobutylene, the first comonomer is substituted, (b) when one of the first and second comonomers is substituted with an ester group containing a polvalkyleneoxy moiety, the other of the first and second comonomers must be substituted, (c) when the second comonomer is sulphonated styrene, the first comonomer is not alkyl acrylate or alkyl methacrylate, and (d) when the first conomoner is maleic anhydride, the second comonomer is not styrene; and (ii) dispersing said formulation in an aqueous medium to form a suspension of the at least one active water-insoluble agrochemical principal.

3. A method according to claim 2 wherein the second comonomer is styrene or substituted styrene.

4. A method according to claim 1 wherein said second comonomer is an α-olefin having at least one polymerizable double bond and at least one cyclic substituent selected from benzene and substituted benzene.

5. A method according to claim 4 wherein the second comonomer is styrene or substituted styrene.

6. A method according to claim 2 wherein the first comonomer is acrylic or methacrylic acid.

7. A method according to claim 1 or 2 wherein the first comonomer is of formula I:

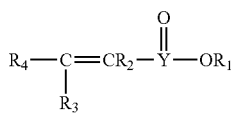

wherein $R_1$ is a metal, quaternary ammonium, phosphonium or sulphonium cation, $R_2$ is hydrogen or $C_1$ alkyl, Y is a carbon atom, $R_3$ is hydrogen and $R_4$ is hydrogen, an alkyl radical or a carboxylic acid derivative of formula II:

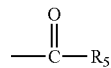

wherein $R_5$ is $OR_6$, $NR_6R_7$ or $SR_6$, where $R_6$ and $R_7$ are hydrogen, alkyl, or alkyl groups with a hetero atom substituent.

8. A method according to claim 1 or 2 wherein the second comonomer is a vinyl compound of formula IV:

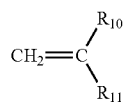

wherein $R_{10}$ is H and $R_{11}$ is given by formula V:

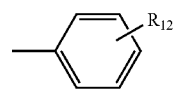

wherein $R_{12}$ represents one or more alkyl radicals or one or more of H, Cl, OR, $SO_3R_1$, $NO_2$ and $PO_3R_1$, where R is a hydrogen atom or alkyl radical having from 1 to 10 carbon atoms (or carboxylated such radical) and $R_1$ is a metal, quaternary ammonium, phosphonium or sulphonium cation.

9. A method according to claim 8 wherein $R_{12}$ is H or an alkyl radical.

10. A method according to claim 8 wherein $R_{12}$ is $SO_3R_1$ or $NO_2$.

11. A method according to claim 10 wherein $R_{12}$ is $SO_3R_1$.

12. A method according to claim 1 or 2 wherein the copolymer contains additional comonomer residues which will not substantially change the character of the polymer.

13. A method according to claim 1 or 2 wherein the at least one water-insoluble agrochemical principal is selected from herbicides, insecticides, fungicides, biocides, molluscicides, algaicides, plant growth regulators, anthelmintics, rodenticides, nematocides, acaricides, amoebicides, protozoacides, crop safeners and adjuvants.

14. A dispersion prepared by the method of claim 1.
15. A dispersion prepared by the method of claim 2.
16. A dispersion prepared by the method of claim 5.
17. A dispersion prepared by the method of claim 6.
18. A method of treating a plant or other agricultural medium comprising spraying said plant or medium with a dispersion formed according to claim 1 or 2.

19. An agricultural formulations suitable for forming a suspension of a finely divided solid water-insoluble material in water, comprising at least one finely divided solid water-insoluble material and at least one dispersant comprising a water soluble copolymer wherein said copolymer comprises a residue of a first comonomer and a residue of a second comonomer, wherein said first comonomer is acrylic or methacrylic acid and said second comonomer is an α-olefin having at least one polymerizable double bond and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides, sulfonates, esters, amides, and optionally substituted pendent aromatic and heteroaromatic groups wherein said optional substituents are selected from the group consisting of sulfonates, nitrates, phosphates and other substituents derived from reaction with electrophilic reagents; with the provisos that (a) when the second comonomer is sulphonated styrene or sulphonated isobutylene, the first comonomer is substituted, (b) when one of the first and second comonomers is substituted with an ester group containing a polyalkyleneoxy moiety, the other of the first and second comonomers must be substituted and (c) when the second comonomer is suiphonated styrene, the first comonomer is not alkyl acrylate or alkyl methacrylate.

20. An agricultural formulation, suitable for forming a suspension of a finely divided solid water-insoluble material in water, comprising at least one finely divided solid water-insoluble material and at least one dispersant comprising a water soluble copolymer wherein said copolymer comprises a residue of a first comonomer and a residue of a second comonomer, wherein said first comonomer is an α, β-unsaturated oxyacid or anhydride and said second comonomer is an α-olefln having at least one polymerizable double bond and at least one cyclic substituent selected from benzene and substituted benzene, and wherein at least one of said first comonomer and said second comonomer is substituted, wherein the substituents for said first comonomer are selected from the group consisting of esters, amides, thioesters and other functional groups derived from reaction with nucleophilic reagents and wherein the substituents for the second comonomer are selected from the group consisting of epoxides, sulfonates, esters, amides, and optionally substituted pendent aromatic and heteroaromatic groups wherein said optional substituents are selected from the group consisting of sulfonates, nitrates, phosphates and other substituents derived from reaction with electrophilic reagents; with the provisos that (a) when the second comonomer is sulphonated styrene or sulphonated isobutylene, the first comonomer is substituted, (b) when one of the first and second comonomers is substituted with an ester group containing a polyalkyleneoxy moiety, the other of the first and second comonomers must be substituted, (c) when the second comonomer is suiphonated styrene, the first comonomer is not alkyl acrylate or alkyl methacrylate, and (d) when the first comonomer is maleic anhydride, the second comonomer is not styrene.

21. An agrochemical formulation according to claim 20 wherein the second comonomer is styrene or substituted styrene.

22. An agrochemical formulation according to claim 19 wherein said second comonomer is an α-olefin having at least one polymerizable double bond and at least one cyclic substituent selected from benzene and substituted benzene.

23. An agrochemical formulation according to claim 22 wherein the second comonomer is styrene or substituted styrene.

24. An agrochemical formulation according to claim 20 wherein the first comonomer is acrylic or methacrylic acid.

25. An agrochemical formulation according to claim 19 or 20 wherein the first comonomer is of formula I:

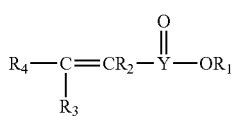

I wherein $R_1$ is a metal, quatenary ammonium, phosphonium or sulphonium cation, $R_2$ is hydrogen or $C_1$ alkyl, Y is a carbon atom, $R_3$ is hydrogen and $R_4$ is hydrogen, an alkyl radical or a carboxylic acid derivative of formula II:

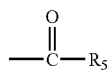

II wherein $R_5$ is $OR_6$, $NR_6R_7$ or $SR_6$, where $R_6$ and $R_7$ are hydrogen, alkyl, or alkyl groups with a hetero atom substituent.

26. An agro chemical formulation according to claim 19 or 20 wherein the second comonomer is a vinyl compound of formula IV:

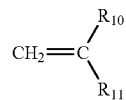

IV wherein $R_{10}$ is H and $R_{11}$ is given by formula V:

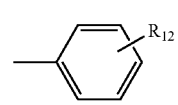

V wherein $R_{12}$ represents one or more alkyl radicals or one or more of H, Cl, OR, $SO_3R_1$, $NO_2$ and $PO_3R_1$, where R is a hydrogen atom or alkyl radical having from 1 to 10 carbon atoms (or carboxylated such radical) and $R_1$ is a metal, quaternary ammonium, phosphonium or sulphonium cation.

27. An agrochemical formulation according to claim 26 wherein $R_{12}$ is H or an alkyl radical.

28. An agro chemical formulation according to claim 26 wherein $R_{12}$ is $SO_3R_1$ or $NO_2$.

29. An agrochemical formulation according to claim 28 wherein $R_{12}$ is $SO_3R_1$.

30. An agrochemical formulation according to claim 19 or 20 wherein the copolymer contains additional comonomer residues which will not substantially change the character of the polymer.

31. An agrochemical formulation according to claim 19 or 20 wherein the at least one water-insoluble material is selected from herbicides, insecticides, fungicides, biocides, molluscicides, algaicides, plant growth regulators, anthelmintics, rodenticides, nematocides, acaricides, amoebicides, protozoacides, crop safeners and adjuvants.

32. An agrochemical formulation according to claim 19 or 20 in the form of a wettable powder.

33. An agrochemical formulation according to claim 19 or 20 in the form of a water dispersible granule.

34. An agrochemical formulation according to claim 19 or 20 in the form of a suspension concentrate.

35. An agrochemical formulation according to claim 19 or 20 further comprising a wetting agent.

* * * * *

UNITED STATES PATENT AND TRADEMARK OFFICE
CERTIFICATE OF CORRECTION

PATENT NO. : 7,109,267 B2
APPLICATION NO. : 10/987094
DATED : September 19, 2006
INVENTOR(S) : Andrew Francis Kirby et al.

Page 1 of 1

It is certified that error appears in the above-identified patent and that said Letters Patent is hereby corrected as shown below:

Column 20
Line 35, "polvalkyleneoxy" should read as --polyalkyleneoxy--.

Column 21
Line 6, "polvalkyleneoxy" should read as --polyalkyleneoxy--.
Line 35, "quatemary" should read as --quaternary--.

Column 22
Line 5, "quatemary" should read as --quaternary--.
Line 28, "formulations" should read as --formulation,--.
Line 55, "suiphonated" should read as --sulphonated--.

Column 23
Line 18, "suiphonated" should read as --sulphonated--.
Line 43, "quatenary" should read as --quaternary--.

Column 24
Line 1, "agro chemical" should read as --agrochemical--.
Line 30, "agro chemical" should read as --agrochemical--.

Signed and Sealed this

Twentieth Day of January, 2009

JON W. DUDAS
*Director of the United States Patent and Trademark Office*